US008927787B2

(12) United States Patent
Warner et al.

(10) Patent No.: US 8,927,787 B2
(45) Date of Patent: Jan. 6, 2015

(54) PROCESS FOR CONTROLLING A REBOILER DURING ALCOHOL RECOVERY AND REDUCED ESTER FORMATION

(75) Inventors: R. Jay Warner, Houston, TX (US); Emily Duff, League City, TX (US); Victor J. Johnston, Houston, TX (US); David Lee, Seabrook, TX (US); Adam Orosco, Houstin, TX (US)

(73) Assignee: Celanese International Corporation, Dallas, TX (US)

( * ) Notice: Subject to any disclaimer, the term of this patent is extended or adjusted under 35 U.S.C. 154(b) by 442 days.

(21) Appl. No.: 13/457,100

(22) Filed: Apr. 26, 2012

(65) Prior Publication Data

US 2012/0277495 A1 Nov. 1, 2012

Related U.S. Application Data

(63) Continuation-in-part of application No. 13/292,914, filed on Nov. 9, 2011, and a continuation-in-part of application No. 13/094,588, filed on Apr. 26, 2011, now Pat. No. 8,686,200.

(60) Provisional application No. 61/576,190, filed on Dec. 15, 2011.

(51) Int. Cl.
C07C 29/149 (2006.01)
C07C 29/80 (2006.01)
C07C 27/04 (2006.01)
C07C 51/12 (2006.01)

(52) U.S. Cl.
CPC ............. C07C 51/12 (2013.01); C07C 29/149 (2013.01); C07C 29/80 (2013.01)
USPC ............................ 568/885; 568/913; 568/918

(58) Field of Classification Search
CPC ........ C07C 29/149; C07C 27/04; C07C 29/80
USPC .......................................... 568/885, 913, 918
See application file for complete search history.

(56) References Cited

U.S. PATENT DOCUMENTS

| | | |
|---|---|---|
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,769,329 A | 10/1973 | Paulik et al. |
| 3,990,952 A | 11/1976 | Katzen et al. |
| 4,126,539 A | 11/1978 | Derr, Jr. et al. |
| 4,149,940 A | 4/1979 | Pinto |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,352,940 A | 10/1982 | Adelman et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,451,677 A | 5/1984 | Bradley et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer et al. |
| 4,626,321 A | 12/1986 | Grethlein et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,842,693 A | 6/1989 | Wheldon |
| 4,886,905 A | 12/1989 | Larkins et al. |
| 4,908,477 A | 3/1990 | Hartmann et al. |
| 4,961,826 A | 10/1990 | Grethlein et al. |
| 4,978,778 A | 12/1990 | Isshiki et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,198,592 A | 3/1993 | Van Beijnum et al. |

(Continued)

FOREIGN PATENT DOCUMENTS

| | | |
|---|---|---|
| CN | 201768393 | 3/2011 |
| CN | 102228831 | 11/2011 |

(Continued)

OTHER PUBLICATIONS

International Preliminary Report on Patentability for PCT/US2012/035220 mailed Nov. 7, 2013.

(Continued)

*Primary Examiner* — Elvis O Price

(57) ABSTRACT

The present invention is related to processes for the separation of ethanol from a crude ethanol product obtained from the hydrogenation of acetic acid. The crude ethanol product is separated in one or more columns. A reboiler is used following one or more of the columns for reducing ester formation.

20 Claims, 4 Drawing Sheets

(56) References Cited

U.S. PATENT DOCUMENTS

| | | |
|---|---|---|
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,414,161 A | 5/1995 | Uhm et al. |
| 5,415,741 A | 5/1995 | Berg |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,502,248 A | 3/1996 | Funk et al. |
| 5,567,765 A | 10/1996 | Moore et al. |
| RE35,377 E | 11/1996 | Steinberg et al. |
| 5,599,976 A | 2/1997 | Scates et al. |
| 5,770,770 A | 6/1998 | Kim et al. |
| 5,800,681 A | 9/1998 | Berg |
| 5,821,111 A | 10/1998 | Gaddy et al. |
| 5,861,530 A | 1/1999 | Atkins et al. |
| 5,973,193 A | 10/1999 | Crane et al. |
| 5,993,610 A | 11/1999 | Berg |
| 6,040,474 A | 3/2000 | Jobson et al. |
| 6,093,845 A | 7/2000 | Van Acker et al. |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,375,807 B1 | 4/2002 | Nieuwoudt et al. |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,223,886 B2 | 5/2007 | Scates et al. |
| 7,226,886 B2 | 6/2007 | Jayaratne et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,732,173 B2 | 6/2010 | Mairal et al. |
| 7,744,727 B2 | 6/2010 | Blum et al. |
| 7,834,223 B2 | 11/2010 | Atkins et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 8,071,821 B2 | 12/2011 | Johnston et al. |
| 2003/0013908 A1 | 1/2003 | Horan et al. |
| 2003/0077771 A1 | 4/2003 | Verser et al. |
| 2006/0019360 A1 | 1/2006 | Verser et al. |
| 2006/0106246 A1 | 5/2006 | Warner et al. |
| 2006/0127999 A1 | 6/2006 | Verser et al. |
| 2007/0031954 A1 | 2/2007 | Mairal et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0221725 A1 | 9/2009 | Chornet et al. |
| 2009/0270651 A1 | 10/2009 | Zinobile et al. |
| 2009/0274480 A1 | 11/2009 | Zona |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0137630 A1 | 6/2010 | Garton et al. |
| 2010/0197485 A1 | 8/2010 | Johnston et al. |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0098501 A1 | 4/2011 | Johnston et al. |
| 2011/0190547 A1 | 8/2011 | Jevtic et al. |
| 2011/0190548 A1 | 8/2011 | Jevtic et al. |
| 2011/0275861 A1 | 11/2011 | Johnston et al. |
| 2011/0275862 A1 | 11/2011 | Johnston et al. |
| 2012/0010437 A1 | 1/2012 | Jevtic |
| 2012/0010438 A1 | 1/2012 | Lee et al. |
| 2012/0010445 A1 | 1/2012 | Johnston et al. |
| 2012/0277481 A1 | 11/2012 | Warner |

FOREIGN PATENT DOCUMENTS

| | | |
|---|---|---|
| CN | 102229520 | 11/2011 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0990638 | 4/2000 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| JP | 6-116182 | 4/1994 |
| JP | 2001-046874 | 2/2001 |
| WO | WO 83/03409 | 10/1983 |
| WO | WO 02/092541 | 11/2002 |
| WO | WO 2005/102513 | 11/2005 |
| WO | WO 2007/003897 | 1/2007 |
| WO | WO 2008/135192 | 11/2008 |
| WO | WO 2009/009320 | 1/2009 |

(56) References Cited

FOREIGN PATENT DOCUMENTS

| | | |
|---|---|---|
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO 2009/105860 | 9/2009 |
| WO | WO 2010/014151 | 2/2010 |
| WO | WO 2010/055285 | 5/2010 |
| WO | WO 2011/053365 | 5/2011 |
| WO | WO 2011/097193 | 8/2011 |
| WO | WO 2011/097219 | 8/2011 |
| WO | WO 2011/097220 | 8/2011 |
| WO | WO 2011/097227 | 8/2011 |
| WO | WO 2011/140485 | 11/2011 |
| WO | WO 2012/006219 | 1/2012 |
| WO | WO 2012/006228 | 1/2012 |
| WO | WO 2012/006499 | 1/2012 |

OTHER PUBLICATIONS

Jakobsson, et al., "Modelling of a side reactor configuration combining reaction and distillation", Chemical Engineering Science, vol. 57, No. 9, May 1, 2002, pp. 1521-1524.

Xu, et al., "Kinetics of acetic acid esterification over ion exchange catalysts", Canadian Journal of Chemical Engineering, vol. 74, Aug. 1, 1996, pp. 493-500.

International Search Report and Written Opinion for PCT/US2012/035198 mailed Oct. 30, 2012.

International Search Report and Written Opinion for PCT/US2012/035208 mailed Nov. 9, 2012.

International Search Report and Written Opinion for PCT/US2012/035271 mailed Nov. 12, 2012.

International Search Report and Written Opinion for PCT/US2012/035194 mailed Nov. 15, 2012.

International Search Report and Written Opinion for PCT/US2012/035175 mailed Nov. 15, 2012.

International Search Report and Written Opinion for PCT/US2011/059889 mailed Jul. 6, 2012.

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Witzeman and Agreda in "Acetic Acid and its Derivatives,", Marcel Dekker, NY, 1992, p. 271.

J. Jones, et al., "The Cativa™ Process for the Manufacture of Acetic Acid", Platinum Metals Review, vol. 44, No. 3, pp. 94-104 (Jul. 2000).

International Search Report and Written Opinion mailed Jul. 6, 2012 in corresponding International Application No. PCT/US2011/059889.

Hidetoshi Kita et al., "Synthesis of a zeolite NaA membrane for pervaporation of water/organic liquid mixtures", Journal of Materials Science Letters, 14 (1995) 206-208.

Marian Simo et al., "Adsorption/Desorption of Water and Ethanol on 3A Zeolite in Near-Adiabatic Fixed Bed", Ind. Eng. Chem. Res., 2009, 48, 9247-9260.

N. Calvar et al., "Esterification of acetic acid with ethanol: Reaction kinetics and operation in a packed bed reactive distillation column", Chemical Engineering and Processing, 46 (207) 1317-1323.

International Search Report and Written Opinion mailed Jun. 29, 2012 in corresponding International Application No. PCT/US2011/060014.

H. Constantin et al., "Influence of C-Sources on the Denitrification Rate of a High-Nitrate Concentrated Industrial Wastewater", Wat. Res. vol. 31, No. 3, 1997, pp. 583-589.

International Search Report and Written Opinion mailed Apr. 19, 2012 in corresponding International Application No. PCT/US2011/060019.

Y. Zhu et al., "Techno-economic Analysis for the Thermochemical Conversion of Lignocellulosic Biomass to Ethanol via Acetic Acid Synthesis", Apr. 1, 2009, pp. 1-71 (80 Pages).

International Search Report and Written Opinion mailed Jul. 30, 2012 in corresponding International Application No. PCT/US2012/035189.

International Search Report and Written Opinion mailed Aug. 2, 2012 in corresponding International Application No. PCT/US2012/035220.

International Search Report and Written Opinion mailed Aug. 6, 2012 in corresponding International Application No. PCT/US2012/035196.

Anonymous, "Studies in Extractive and Azeotropic Distillation Series: Study No. 4—Separation of Alcohols from the Acetate/Alcohol/Water Ternary by Extractive Distillation", May 9, 2008, pp. 1-9.

V. Ragaini et al., "Increasing the value of dilute acetic acid streams through esterification Part 1. Experimental analysis of the reaction zone", Applied Catalysis B: Environmental, vol. 64, 2006, pp. 66-71.

International Search Report and Written Opinion mailed Jul. 11, 2012 in corresponding International Application No. PCT/US2012/035203.

International Search Report and Written Opinion mailed Jul. 30, 2012 in corresponding International Application No. PCT/US2012/035273.

Tracy J. Benson et al., "Cellulose Based Adsorbent Materials for the Dehydration of Ethanol Using Thermal Swing Adsorption", Adsorption, vol. 11, 2005, pp. 697-701.

Yu Huang et al., "Low-Energy Distillation-Membrane Separation Process", Ind. Eng. Chem. Res., vol. 49, 2010, pp. 3760-3768.

International Search Report and Written Opinion for PCT/US2011/023276 mailed Sep. 2, 2011.

Response to Final Office Action for U.S. Appl. No. 13/094,488, filed Oct. 18, 2013.

Response to Final Office Action for U.S. Appl. No. 13/094,661, filed Nov. 25, 2013.

PROCESS FOR CONTROLLING A REBOILER DURING ALCOHOL RECOVERY AND REDUCED ESTER FORMATION

CROSS REFERENCE TO RELATED APPLICATION

This application claims priority to U.S. Prov. App. No. 61/576,190, filed on Dec. 15, 2011, the entire contents and disclosures of which are incorporated herein by reference. This application is also a continuation-in-part of U.S. application Ser. No. 13/292,914, filed on Nov. 9, 2011, and U.S. application Ser. No. 13/094,588, filed on Apr. 26, 2011, the entire contents and disclosures of which are incorporated herein by reference.

FIELD OF THE INVENTION

The present invention relates generally to processes for producing alcohol, preferably ethanol. In particular, the present invention is directed to a process for controlling a reboiler to reduce ester formation.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulosic materials, such as corn or sugar cane. Conventional methods for producing ethanol from organic feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic materials, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acids, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition, when conversion is incomplete, acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

U.S. Pat. No. 7,842,844 describes a process for improving selectivity and catalyst activity and operating life for the conversion of hydrocarbons to ethanol and optionally acetic acid in the presence of a particulate catalyst, said conversion proceeding via a syngas generation intermediate step.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising hydrogenating acetic acid and/or an ester thereof in a reactor in the presence of a catalyst to form a crude ethanol product; separating at least a portion of the crude ethanol product in a first distillation column to yield a first distillate comprising acetaldehyde and ethyl acetate and a tower bottoms comprising ethanol, acetic acid and water; feeding a first portion of the tower bottoms to a reboiler to generate a reboiler vapor stream; withdrawing a second portion of the tower bottoms as a first residue comprising less than 1.5 wt. % ethyl acetate, preferably less than 1.1 wt. % or less than 1 wt. %, and separating at least a portion of the first residue in a second distillation column to yield a second residue comprising acetic acid and water and a second distillate comprising ethanol and ethyl acetate; and separating at least a portion of the second distillate to yield a third residue comprising ethyl acetate and a third residue comprising ethanol. The reboiler may be selected from the group consisting of internal reboiler, kettle reboiler, jacketed kettle reboiler, thermosyphon reboiler, falling film reboiler, fire reboiler, and forced circulation reboiler. In some embodiments, at least a portion of the first distillate and/or third distillate may be returned to the reactor. The first distillate, second distillate, and/or third distillate may be separated to form an ethanol stream and a raffinate stream comprising ethyl acetate, wherein the ethanol stream may be fed to the third distillation column and/or combined with the third residue. At least a portion of the raffinate stream may be returned to the reactor. In some embodiments, the second distillate may be substantially free of acetic acid.

In exemplary embodiments of the present invention, the reboiler may be a kettle reboiler. Although these embodiments use kettle reboilers, it should be understood that other suitable reboilers may be used. In a second embodiment, the present invention is directed to a process for producing ethanol, comprising hydrogenating acetic acid and/or an ester thereof in a reactor in the presence of a catalyst to form a crude ethanol product, and separating at least a portion of the crude ethanol product in a first distillation column to yield a first distillate comprising acetaldehyde and ethyl acetate and a tower bottoms comprising ethanol, acetic acid, and water. The tower bottoms comprises at least 50% of the ethanol in the crude ethanol product. The process further comprises feeding the tower bottoms to a kettle reboiler to generate a reboiler vapor stream, and a residue product, wherein ethyl acetate is formed in the reboiler and the residue product comprises less than 1.5 wt. % ethyl acetate, e.g., less than 1.1 wt. % or less than 1 wt. %, separating at least a portion of the residue product in a second distillation column to yield a second residue comprising acetic acid and water and a second distillate comprising ethanol, and ethyl acetate, and separating at least a portion of the second distillate to yield a third distillate comprising ethyl acetate and a third residue comprising ethanol. The second distillate may be substantially free of acetic acid. In one embodiment, at least a portion of the third distillate to the first distillation column.

In one embodiment, a portion of the second residue may be recovered and returned to reactor. In another embodiment, a portion of the second residue may be directed to a waste water treatment facility to feed microorganisms used in the waste water treatment facility. In still another embodiment, the acetic acid in the portion of the second residue may be neutralizing or reacted to form an ester.

In a third embodiment, the present invention is directed to a process for producing ethanol, comprising providing a crude ethanol product comprising ethanol, acetic acid, ethyl acetate, acetaldehyde, and water, separating a portion of the crude ethanol product in a first distillation column to yield a first distillate comprising acetaldehyde and ethyl acetate and a tower bottoms comprising ethanol, acetic acid, and water, feeding the tower bottoms to a kettle reboiler to generate a reboiler vapor stream, and a residue product, wherein ethyl acetate is formed in the reboiler and the residue product comprises less than 1.5 wt. % ethyl acetate, separating a portion of the residue product in a second distillation column to yield a second residue comprising acetic acid and water and a second distillate comprising ethanol and ethyl acetate, and separating at least a portion of the second distillate to yield a third distillate comprising ethyl acetate and a third residue comprising ethanol.

In a fourth embodiment, the present invention is directed to a process for producing ethanol comprising providing a crude ethanol product comprising ethanol, ethyl acetate, acetaldehyde, and water, separating at least a portion of the crude ethanol product in a first distillation column to form a first distillate comprising acetaldehyde and ethyl acetate and a tower bottoms comprising ethanol and water, feeding the tower bottoms to a kettle reboiler to generate a reboiler vapor stream, and a residue product, wherein ethyl acetate is formed in the reboiler and the residue product comprises less than 1.5 wt. % ethyl acetate, separating a portion of the residue product in a second distillation column to yield a second residue comprising acetic acid and water and a second distillate comprising ethanol and ethyl acetate, separating at least a portion of the second distillate to form an organic stream comprising ethyl acetate and ethanol and an aqueous stream comprising water, and separating the organic stream in a third distillation column to form a third distillate comprising ethyl acetate and a third residue comprising ethanol.

In a fifth embodiment, the present invention is directed to a process for producing ethanol comprising hydrogenating acetic acid and/or an ester thereof in a reactor in the presence of a catalyst to form a crude ethanol product; separating a portion of the crude ethanol product in a first distillation column to yield a first distillate comprising acetaldehyde and ethyl acetate and a tower bottoms comprising ethanol, acetic acid and water, feeding the tower bottoms to a kettle reboiler to generate a reboiler vapor stream, and a residue product, wherein ethyl acetate is formed in the reboiler and the residue product comprises less than 1.5 wt. % ethyl acetate, separating a portion of the residue product in a second distillation column to yield a second residue comprising acetic acid and a second distillate comprising ethanol, ethyl acetate and water, removing water from at least a portion of the second distillate to yield an ethanol product stream having a lower water content than the at least a portion of the second distillate, and separating at least a portion of the ethanol product stream in a third distillation column to yield a third distillate comprising ethyl acetate and a third residue comprising ethanol and less than 8 wt. % water, e.g., less than 3 wt. % water or less than 1 wt. % water. In one embodiment, the water is removed using a water separation unit selected from the group consisting of an adsorption unit, membrane, extractive column distillation, molecular sieves, or a combination thereof.

In a sixth embodiment, the present invention is directed to a process for producing ethanol comprising hydrogenating acetic acid and/or an ester thereof in a reactor in the presence of a catalyst to form a crude ethanol product; separating a portion of the crude ethanol product in a first distillation column to yield a first distillate comprising acetaldehyde and ethyl acetate and a tower bottoms comprising ethanol, and acetic acid, feeding the tower bottoms to a kettle reboiler to generate a reboiler vapor stream, and a residue product, wherein ethyl acetate is formed in the reboiler and the residue product comprises less than 1.5 wt. % ethyl acetate, separating a portion of the residue product in a second distillation column to yield a second residue comprising high boiling point components selected from the group consisting of acetic acid, water, alcohols having more than 2 carbon atoms, and mixtures thereof and a second distillate comprising ethanol and ethyl acetate, and separating at least a portion of the second distillate to yield a third distillate comprising ethyl acetate and a third residue comprising ethanol; wherein the residue product comprises more ethyl acetate than the tower bottoms.

In a seventh embodiment, the present invention is directed to a process for producing ethanol, comprising hydrogenating acetic acid and/or an ester thereof in a reactor in the presence of a catalyst to form a crude ethanol product, separating a portion of the crude ethanol product in a first distillation column to yield a first distillate comprising acetaldehyde and ethyl acetate and a tower bottoms comprising ethanol, acetic acid, and water, extracting a portion of the first distillate to yield an ethanol stream and a raffinate stream comprising ethyl acetate, feeding the tower bottoms to a kettle reboiler to generate a reboiler vapor stream, and a residue product, wherein ethyl acetate is formed in the reboiler and the residue product comprises less than 1.5 wt. % ethyl acetate, separating a portion of the residue product in a second distillation column to yield a second residue comprising acetic acid and water and a second distillate comprising ethanol and ethyl acetate, and separating at least a portion of the second distillate to yield a third distillate comprising ethyl acetate and a third residue comprising ethanol. In one embodiment, at least a portion of the raffinate stream is returned to the reactor.

In an eighth embodiment, the present invention is directed to a process for producing ethanol, comprising hydrogenating acetic acid and/or an ester thereof in a reactor in the presence of a catalyst to form a crude ethanol product, separating a portion of the crude ethanol product in a first distillation column to yield a first distillate comprising acetaldehyde and ethyl acetate and a tower bottoms comprising ethanol, acetic acid, and water, feeding the tower bottoms to a kettle reboiler to generate a reboiler vapor stream, and a residue product, wherein ethyl acetate is formed in the reboiler and the residue product comprises less than 1.5 wt. % ethyl acetate, separating a portion of the residue product in a second distillation column to yield a second residue comprising acetic acid and water and a second distillate comprising ethanol and ethyl acetate, separating at least a portion of the second distillate to yield a third distillate comprising ethyl acetate and a third residue comprising ethanol, and extracting a portion of the third distillate to yield an ethanol stream and a raffinate stream comprising ethyl acetate.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

The present invention relates to processes for recovering ethanol produced by hydrogenating acetic acid in the presence of a catalyst. The hydrogenation reaction produces a crude ethanol product that comprises ethanol, water, ethyl acetate, acetaldehyde, acetic acid, and other impurities. The processes of the present invention involve separating the crude ethanol product in a first column into a tower bottoms comprising ethanol, water, and acetic acid. The first column operates to remove a majority of the light organics, including ethyl acetate and acetaldehyde. The tower bottoms may comprise very low amounts of ethyl acetate, e.g., less than 1 wt. % based on the total tower bottoms, e.g., less than 0.5 wt. %, or less than 0.1 wt. %. In terms of ranges, the ethyl acetate concentration in tower bottoms may be from 0.001 to 1 wt. %, e.g., from 0.01 to 0.5 wt. % or from 0.01 to 0.1 wt. %. A portion of the tower bottoms is introduced to reboiler to produce a vapor return stream for driving separation within the column. When the reboiler conditions are not controlled, there may be an increase of ethyl acetate in the column, which further increases the amount of ethyl acetate in the residue product. If the reboiler conditions are not controlled, then the operating function of the first column, i.e. to remove light organics, may be less efficient and further separation may be required to remove the ethyl acetate. Ethyl acetate preferably is further separated from ethanol to obtain a suitable ethanol product for industrial or fuel use. In one embodiment, the process involves controlling the reboiler so that low amounts of ethyl acetate are formed in the reboiler, preferably less than 1.5 wt. % of the residue product comprises ethyl acetate, e.g., less than 1.1 wt. %. In terms of ranges, the ethyl acetate concentration in tower bottoms may be from 0.01 to 1.5 wt. %, e.g., from 0.1 to 1.4 wt. % or from 0.5 to 1.1 wt. %. Generally, there is a relatively larger concentration of ethyl acetate in the residue product than the tower bottoms.

Figure 1:
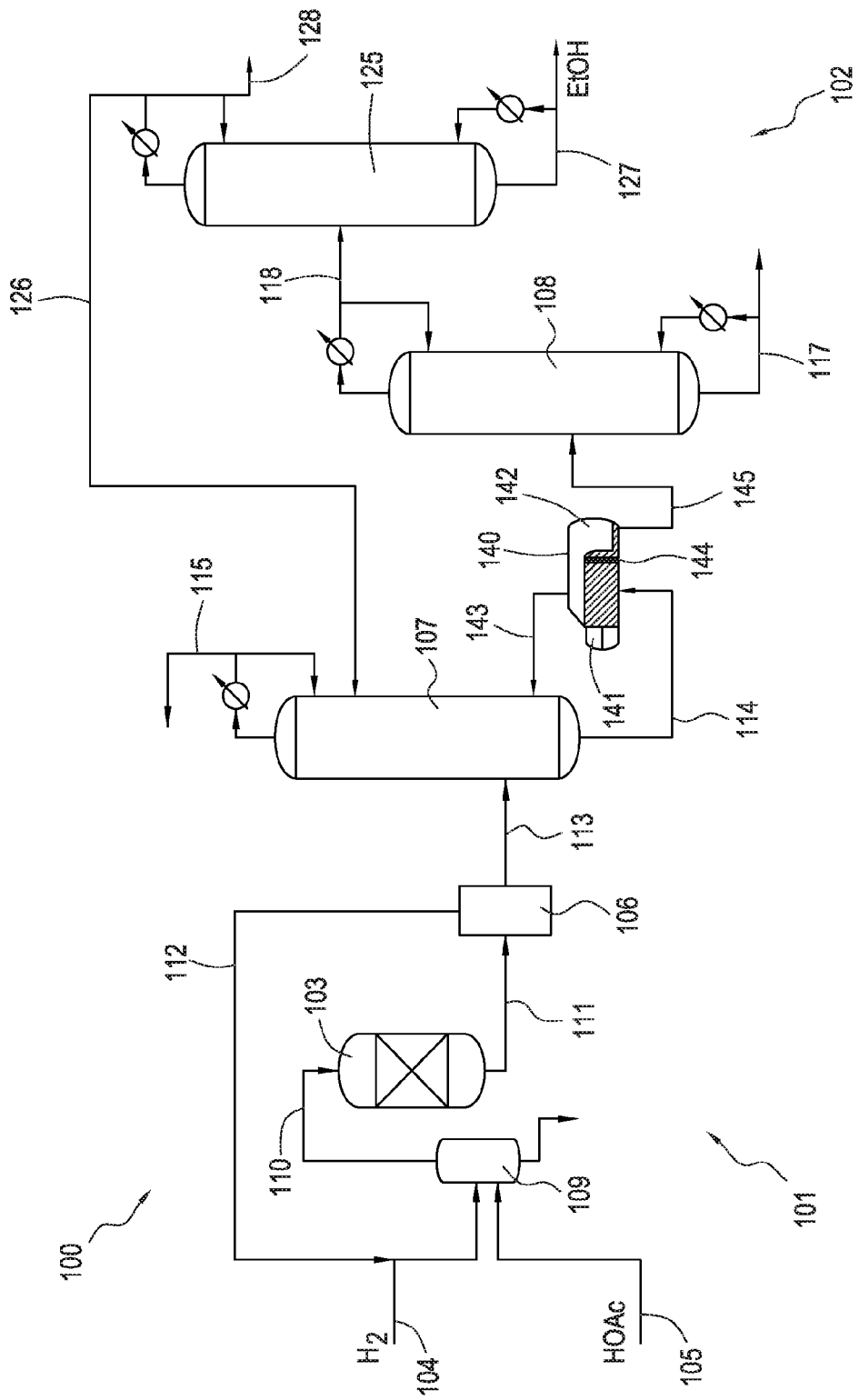
FIG. 1 is a schematic diagram of an ethanol production system with multiple distillation columns to recover ethanol including a kettle reboiler in accordance with one embodiment of the present invention.

In one embodiment, the reboiler of the present invention transfers energy so that the liquid tower bottoms is transferred to a boiling point. Suitable reboilers may include, but are not limited to, an internal reboiler, kettle reboiler, jacketed kettle reboiler, thermosyphon reboiler, falling film reboiler, fire reboiler, and forced circulation reboiler. The reboiler may be electrically heated, steam heated, or heated with a hot liquid or hot oil. In a preferred embodiment, the first column has a steam heated kettle reboiler. As explained below, FIG. 1 shows an exemplary kettle reboiler. It is understood that other exemplary reboilers may be used. Thermosyphon reboilers may include recirculating reboilers, which may be vertical or horizontal, and which may further be baffled or unbaffled. Thermosyphon reboilers may also include once-through reboilers, which may be vertical or horizontal. Advantages of using a kettle reboiler may include ease of maintenance and control, and no limit on vapor load. Advantages of using a thermosyphon reboiler include lower cost than a kettle reboiler.

Generally, when the reboiler supplies too much heat through the vapor return stream, the distillation column may flood. Also, too little heat through the vapor return stream may cause the separation efficiency of the distillation column to decrease. In addition, due to the composition of the tower bottoms, e.g., ethanol, acetic acid, and water, the esterification equilibrium may also favor formation of ethyl acetate. This esterification reaction may be promoted when the tower bottoms is heated. To control the ethyl acetate production, the reboiler is operated to maintain low ethyl acetate formation and provide sufficient energy to separate the crude ethanol product. This may include controlling residence time in the reboiler. Without being limited by theory, it is believed that as residence time increases, ethyl acetate formation increases.

In recovering ethanol, the processes of the present invention use one or more distillation columns. In preferred embodiments, the residue product comprises a substantial portion of the ethanol, water and acetic acid from the crude ethanol product. Residue product refers generally to a stream that exits from the base or lower portion of a distillation column. In some embodiments, the residue may be fed directly or indirectly to an additional distillation column. The residue product from the reboiler, as shown in FIG. 1, for example, may comprise at least 50% of the ethanol from the crude ethanol product, and more preferably at least 70%. In terms of ranges, the residue product may comprise from 50% to 99.9% of the ethanol from the crude ethanol product, and more preferably from 70% to 99.9%. In other embodiments, the residue product may be withdrawn from the base of the distillation column, and preferably separate from the tower bottoms. The amount of ethanol from the crude ethanol recovered in the residue product may be greater than 97.5%, e.g. greater than 99.9%. Preferably, the residue product comprises less than 1.5 wt. % ethyl acetate, e.g., less than 1.1 wt. %. As described herein for exemplary kettle reboilers, even though the tower bottoms may comprise very low amounts of ethyl acetate, some ethyl acetate may be formed in the reboiler. The present invention controls the reboiler process so that ethyl acetate does not increase to point that makes the operation of the first column inefficient.

In preferred embodiments, the residue product may also comprise a substantial portion of the water and the acetic acid from the crude ethanol product. The residue product may comprise at least 80% of the water from the crude ethanol product, and more preferably at least 90%. In terms of ranges, the residue product preferably comprises from 80% to about 100% of the water from the crude ethanol product, and more preferably from 90% to 99.4%. The residue product may comprise at least 85% of the acetic acid from the crude ethanol product, e.g., at least 90% and more preferably about 100%. In terms of ranges, the residue product preferably comprises from 85% to about 100% of the acetic acid from the crude ethanol product, and more preferably from 90% to 99.9%. In one embodiment, substantially all of the acetic acid is recovered in the residue product.

The residue product comprising ethanol, ethyl acetate, water, and acetic acid may be further separated to recover ethanol. In one preferred embodiment, the water and acetic acid may be removed as another residue stream in a separate distillation column. Ethanol and ethyl acetate may be separated in another column, if necessary to remove ethyl acetate from the ethanol product. In addition, the water carried over in the separate distillation column may be removed with a water separator that is selected from the group consisting of an adsorption unit, membrane, extractive column distillation, molecular sieves, or a combination thereof.

In one embodiment each of the columns is sized to be capital and economically feasible for the rate of ethanol production. The total diameter for the columns used to separate the crude ethanol product may be from 5 to 40 meters, e.g., from 10 to 30 meters or from 12 to 20 meters. Each column may have a varying size. In one embodiment, the ratio of column diameter in meters for all the distillation columns to tons of ethanol produced per hour is from 1:2 to 1:30, e.g., from 1:3 to 1:20 or from 1:4 to 1:10. This would allow the process to achieve production rates of 25 to 250 tons of ethanol per hour.

The distillate from the initial column comprises light organics, such as acetaldehyde and ethyl acetate, diethyl acetal and acetone. In addition, minor amounts of ethanol and water may be present in the distillate. Removing these components from the crude ethanol product in the initial column provides an efficient means for removing acetaldehyde and ethyl acetate. In addition, acetaldehyde, diethyl acetal, and acetone are not carried over with the ethanol when multiple columns are used, thus reducing the formation of byproducts from acetaldehyde, diethyl acetal, and acetone. In particular, acetaldehyde and/or ethyl acetate may be returned to the reactor, and converted to additional ethanol. In another embodiment, a purge may remove these light organics from the system. The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from other available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from a variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{14}C:^{12}C$ ratio of the methanol, acetic acid and/or ethanol may be from one half to about 1 of the $^{14}C:^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180, and U.S. Pub. Nos. 2008/0193989 and 2009/0281354, the entireties of which are incorporated herein by reference. See also US Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, which is an aqueous solution of lignin residues, hemicellulose, and inorganic chemicals.

U.S. Pat. No. RE 35,377, also incorporated herein by reference, provides a method for the production of methanol by converting carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as a syngas including hydrogen and carbon monoxide, are incorporated herein by reference in their entireties.

Acetic acid fed to the hydrogenation reactor may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its aldehyde, may be beneficial in producing propanol. Water may also be present in the acetic acid feed. Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system so that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2100 kPa. The reactants may be fed to the reactor at a gas hourly space velocity (GHSV) from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds.

The hydrogenation of acetic acid to form ethanol is preferably conducted in the presence of a hydrogenation catalyst. Exemplary catalysts are further described in U.S. Pat. Nos. 7,608,744 and 7,863,489, and U.S. Pub. Nos. 2010/0121114 and 2010/0197985, the entireties of which are incorporated herein by reference. In another embodiment, the catalyst comprises a Co/Mo/S catalyst of the type described in U.S. Pub. No. 2009/0069609, the entirety of which is incorporated herein by reference. In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. In some embodiments, the catalyst may be a bulk catalyst.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %.

Preferred metal combinations for exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, or ruthenium/iron.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. When present, the total weight of the third metal preferably is from 0.05 to 20 wt. %, e.g., from 0.1 to 10 wt. %, or from 0.1 to 7.5 wt. %. In one embodiment, the catalyst may comprise platinum, tin and cobalt.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 99 wt. %, or from 80 to 97.5 wt. %. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof. The support may be a modified support and the support modifier is present in an amount from 0.1 to 50 wt. %, e.g., from 0.2 to 25 wt. %, from 1 to 20 wt. %, or from 3 to 15 wt. %, based on the total weight of the catalyst.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. Preferred support modifiers include oxides of tungsten, molybdenum, and vanadium.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. The basic support modifier may be selected from the group consisting of oxides and metasilicates of any of sodium, potassium, magnesium, calcium, scandium, yttrium, and zinc, as well as mixtures of any of the foregoing. In one embodiment, the basic support modifier is a calcium silicate, such as calcium metasilicate ($CaSiO_3$). The calcium metasilicate may be crystalline or amorphous.

Catalysts on a modified support may include one or more metals from the group of platinum, palladium, cobalt, tin, or rhenium on a silica support modified by one or more modifiers from the group of calcium metasilicate, oxides of tungsten, molybdenum, and vanadium.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197985 referred to above, the entireties of which are incorporated herein by reference.

After the washing, drying and calcining of the catalyst is completed, the catalyst may be reduced in order to activate the catalyst. Reduction is carried out in the presence of a reducing gas, preferably hydrogen. The reducing gas is continuously passed over the catalyst at an initial ambient temperature that is increased up to 400° C. In one embodiment, the reduction is preferably carried out after the catalyst has been loaded into the reaction vessel where the hydrogenation will be carried out.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a percentage based on acetic acid in the feed. The conversion may be at least 40%, e.g., at least 50%, at least 60%, at least 70% or at least 80%. Although catalysts that have high conversions are desirable, such as at least 80% or at least 90%, in some embodiments a low conversion may be acceptable at high selectivity for ethanol.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethanol is at least 60%, e.g., at least 70%, or at least 80%. Preferred embodiments of the hydrogenation process also have low selectivity to undesirable products, such as methane, ethane, and carbon dioxide. The selectivity to these undesirable products preferably is less than 4%, e.g., less than 2% or less than 1%.

The term "productivity," as used herein, refers to the grams of a specified product, e.g., ethanol, formed during the hydrogenation based on the kilograms of catalyst used per hour. The productivity may range from 100 to 3,000 grams of ethanol per kilogram of catalyst per hour.

In various embodiments of the present invention, the crude ethanol product produced by the hydrogenation process, before any subsequent processing, such as purification and separation, will typically comprise acetic acid, ethanol and water. Exemplary compositional ranges for the crude ethanol product are provided in Table 1, excluding hydrogen. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product of Table 1 may have low concentrations of acetic acid with higher conversion, and the acetic acid concentration may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Exemplary ethanol recovery systems in accordance with embodiments of the present invention are shown in FIGS. 1 to 4. Each hydrogenation system 100 provides a suitable hydrogenation reactor and a process for separating ethanol from the crude reaction mixture according to an embodiment of the invention. System 100 comprises reaction zone 101 and separation zone 102. Reaction zone 101 comprises reactor 103, hydrogen feed line 104 and acetic acid feed line 105. Separation zone 102 comprises a separator 106, and one or more distillation columns. For the purposes of explanation, a reboiler 140 is shown in greater detail for first column 107 than the other columns. It should be understood that the other columns have similar reboilers. In addition, for the purposes of explanation, reboiler 140 is shown as a kettle reboiler, but other reboilers may be used within the scope of the present invention.

As shown in FIGS. 1-4, the feed to reactor 103 comprises fresh acetic acid. Hydrogen and acetic acid are fed to a vaporizer 109 via lines 104 and 105, respectively, to create a vapor feed stream in line 110 that is directed to reactor 103. Hydrogen feed line 104 may be pre-heated to a temperature from 30° C. to 150° C., e.g., from 50° C. to 125° C. or from 60° C. to 115° C. Hydrogen feed line 105 may be fed at a pressure from 1300 kPa to 3100 kPa, e.g., from 1500 kPa to 2800 kPa, or 1700 kPa to 2600 kPa. In one embodiment, lines 104 and 105 may be combined and jointly fed to the vaporizer 109. The temperature of the vapor feed stream in line 110 is preferably from 100° C. to 350° C., e.g., from 120° C. to 310° C. or from 150° C. to 300° C. Any feed that is not vaporized is removed from vaporizer 109 via a blowdown stream. In addition, although line 110 is shown as being directed to the top of reactor 103, line 110 may be directed to the side, upper portion, or bottom of reactor 103.

Reactor 103 contains the catalyst that is used in the hydrogenation of the carboxylic acid, preferably acetic acid. In one embodiment, one or more guard beds (not shown) may be used upstream of the reactor, optionally upstream of vaporizer 109, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product is withdrawn, preferably continuously, from reactor 103 via line 111.

The crude ethanol product may be condensed and fed to a separator 106, which, in turn, forms a vapor stream 112 and a liquid stream 113. In some embodiments, separator 106 may comprise a flasher or a knockout pot. Separator 106 may operate at a temperature from 20° C. to 350° C., e.g., from 30° C. to 325° C. or from 60° C. to 250° C. The pressure of separator 106 may be from 100 kPa to 3000 kPa, e.g., from 125 kPa to 2500 kPa or from 150 kPa to 2200 kPa. Optionally, the crude ethanol product in line 111 may pass through one or more membranes to separate hydrogen and/or other non-condensable gases.

Vapor stream 112 exiting separator 106 may comprise hydrogen and hydrocarbons, and may be purged and/or returned to reaction zone 101. As shown, vapor stream 112 is combined with the hydrogen feed 104 and co-fed to vaporizer 109. In some embodiments, the returned vapor stream 112 may be compressed before being combined with hydrogen feed 104.

Liquid stream 113 from separator 106 is withdrawn and directed as a feed composition to the side of first distillation column 107, also referred to as an "acetaldehyde removal column." Liquid stream 113 may be heated from ambient temperature to a temperature of up to 70° C., e.g., up to 50° C., or up to 40° C. The additional energy required to pre-heat liquid stream 113 above 70° C. does not achieve the desired energy efficiency in first column 107 with respect to reboiler duties. In another embodiment, liquid stream 113 is not separately pre-heated, but is withdrawn from separator 106, and cooled if needed, at a temperature of less than 70° C., e.g., less than 50° C., or less than 40° C., and directly fed to first column 107.

In one embodiment, the contents of liquid stream 113 are substantially similar to the crude ethanol product obtained from the reactor, except that the composition has been depleted of hydrogen, carbon dioxide, methane or ethane, which have been removed by separator 106. Accordingly, liquid stream 113 may also be referred to as a crude ethanol product. Exemplary components of liquid stream 113 are provided in Table 2. It should be understood that liquid stream 113 may contain other components, not listed in Table 2.

TABLE 2

COLUMN FEED COMPOSITION (Liquid Stream 113)

| | Conc. (wt. %) | Conc. (wt. %) | Conc. (wt. %) |
|---|---|---|---|
| Ethanol | 5 to 72 | 10 to 70 | 15 to 65 |
| Acetic Acid | <90 | 5 to 80 | 0 to 35 |
| Water | 5 to 40 | 5 to 30 | 10 to 26 |
| Ethyl Acetate | <30 | 0.001 to 25 | 1 to 20 |
| Acetaldehyde | <10 | 0.001 to 3 | 0.1 to 3 |
| Acetal | <5 | 0.01 to 5 | 0.01 to 3 |
| Acetone | <5 | 0.0005 to 0.05 | 0.001 to 0.03 |

The amounts indicated as less than (<) in the tables throughout the present specification are preferably not present and if present may be present in amounts greater than 0.0001 wt. %.

In one embodiment, the ethyl acetate concentration in the liquid stream 113 may affect the first column reboiler duty and size. Decreasing ethyl acetate concentrations may allow for reduced reboiler duty and size. In one embodiment, to reduce the ethyl acetate concentration (a) the catalyst in reactor may convert ethyl acetate in addition to acetic acid; (b) the catalyst may be less selective for ethyl acetate, and/or (c) the feed to reactor, including recycles, may contain less ethyl acetate.

In the embodiment shown in FIG. 1, liquid stream 113 is introduced in the upper part of first column 107, e.g., upper half or upper third. In addition to liquid stream 113 an ethyl acetate recycle stream 126 is also fed to first column. Depending on the ethyl acetate concentration of ethyl acetate recycle stream 126 this stream may be introduced above or near the feed point of the liquid stream 113. Depending on the targeted ethyl acetate concentration in the distillate of first column 107 the feed point of ethyl acetate recycle stream 126 will vary.

Liquid stream 113 and ethyl acetate recycle stream 126 collectively comprise the organic feed to first column 107. In one embodiment, organic feed comprises from 1 to 25% of ethyl acetate recycle stream 126, e.g., from 3% to 20% or from 5% to 15%. This amount may vary depending on the production of reactor 103 and amount of ethyl acetate to be recycled.

In some optional embodiments, an extractive agent, such as water, may also be introduced above liquid stream 113. When used, the extractive agent preferably comprises water that has been retained within the system, such as from a portion of the second residue. The extractive agent may also be a dilute acid stream comprising up to 20 wt. % acetic acid, e.g., up to 10 wt. % acetic acid or up to 5 wt. % acetic acid. In one embodiment, the mass flow ratio of water in extractive agent to the mass flow of the organic feed, which comprises liquid stream 113 and ethyl acetate recycle stream 126, may range from 0.05:1 to 2:1, e.g., from 0.07 to 0.9:1 or from 0.1:1 to 0.7:1.

In one embodiment, first column 107 is a tray column having from 5 to 90 theoretical trays, e.g. from 10 to 60 theoretical trays or from 15 to 50 theoretical trays. The number of actual trays for each column may vary depending on the tray efficiency, which is typically from 0.5 to 0.7 depending on the type of tray. The trays may be sieve trays, fixed valve trays, movable valve trays, or any other suitable design known in the art. In other embodiments, a packed column having structured packing or random packing may be employed.

When first column 107 is operated under 50 kPa, the temperature of the tower bottoms exiting in line 114 preferably is from 20° C. to 100° C., e.g., from 30° C. to 90° C. or from 40° C. to 80° C. The base of column 107 may be maintained at a relatively low temperature by withdrawing a residue stream comprising ethanol, ethyl acetate, water, and acetic acid, thereby providing an energy efficiency advantage. The temperature of the distillate exiting in line 115 from column 107 preferably at 50 kPa is from 10° C. to 80° C., e.g., from 20° C. to 70° C. or from 30° C. to 60° C. The pressure of first column 107 may range from 0.1 kPa to 510 kPa, e.g., from 1 kPa to 475 kPa or from 1 kPa to 375 kPa. In some embodiments, first column 107 may operate under a vacuum of less than 70 kPa, e.g., less than 50 kPa, or less than 20 kPa. Operating under a vacuum may decrease the reboiler duty and reflux ratio of first column 107. However, a decrease in operating pressure for first column 107 does not substantially affect column diameter.

In first column 107, a weight majority of the ethanol, water, acetic acid, are removed from the organic feed, including liquid stream 113 and ethyl acetate recycle stream 126, and are withdrawn, preferably continuously, as tower bottoms in line 114. This includes any water added as an optional extractive agent. Concentrating the ethanol in the residue reduces the amount of ethanol that is recycled to reactor 103 and in turn reduces the size of reactor 103. Preferably less than 10% of the ethanol from the organic feed, e.g., less than 5% or less than 1% of the ethanol, is returned to reactor 103 from first column 107. In addition, concentrating the ethanol also will concentrate the water and/or acetic acid in the residue. In one embodiment, at least 90% of the ethanol from the organic feed is withdrawn in the residue, and more preferably at least 95%. In addition, ethyl acetate may also be present in the tower bottoms in line 114. The reboiler duty may decrease with an ethyl acetate concentration increase in the tower bottoms in line 114. When other reboilers are used, such as thermosyphon reboilers or recirculating reboilers, a portion of tower bottoms in line 114 may be directly fed to second column 108. This portion of tower bottoms in line 114 may be referred to as a residue product.

First column 107 also forms an distillate, which is withdrawn in line 115, and which may be condensed and refluxed, for example, at a ratio from 30:1 to 1:30, e.g., from 10:1 to 1:10 or from 5:1 to 1:5. Higher mass flow ratios of water to organic feed may allow first column 107 to operate with a reduced reflux ratio.

First distillate in line 115 preferably comprises a weight majority of the acetaldehyde and ethyl acetate from liquid stream 113, as well as from ethyl acetate recycle stream 126. In one embodiment, the first distillate in line 115 comprises a concentration of ethyl acetate that is less than the ethyl acetate concentration for the azeotrope of ethyl acetate and water, and more preferably less than 75 wt. %. The overhead distillate stream in line 115 preferably comprises a weight majority of the acetaldehyde and ethyl acetate from liquid stream 113. In some embodiments, tower bottoms comprises less than 1 wt. % ethyl acetate, e.g., less than 0.5 wt. % or less than 0.2 wt. % ethyl acetate.

Figure 3:
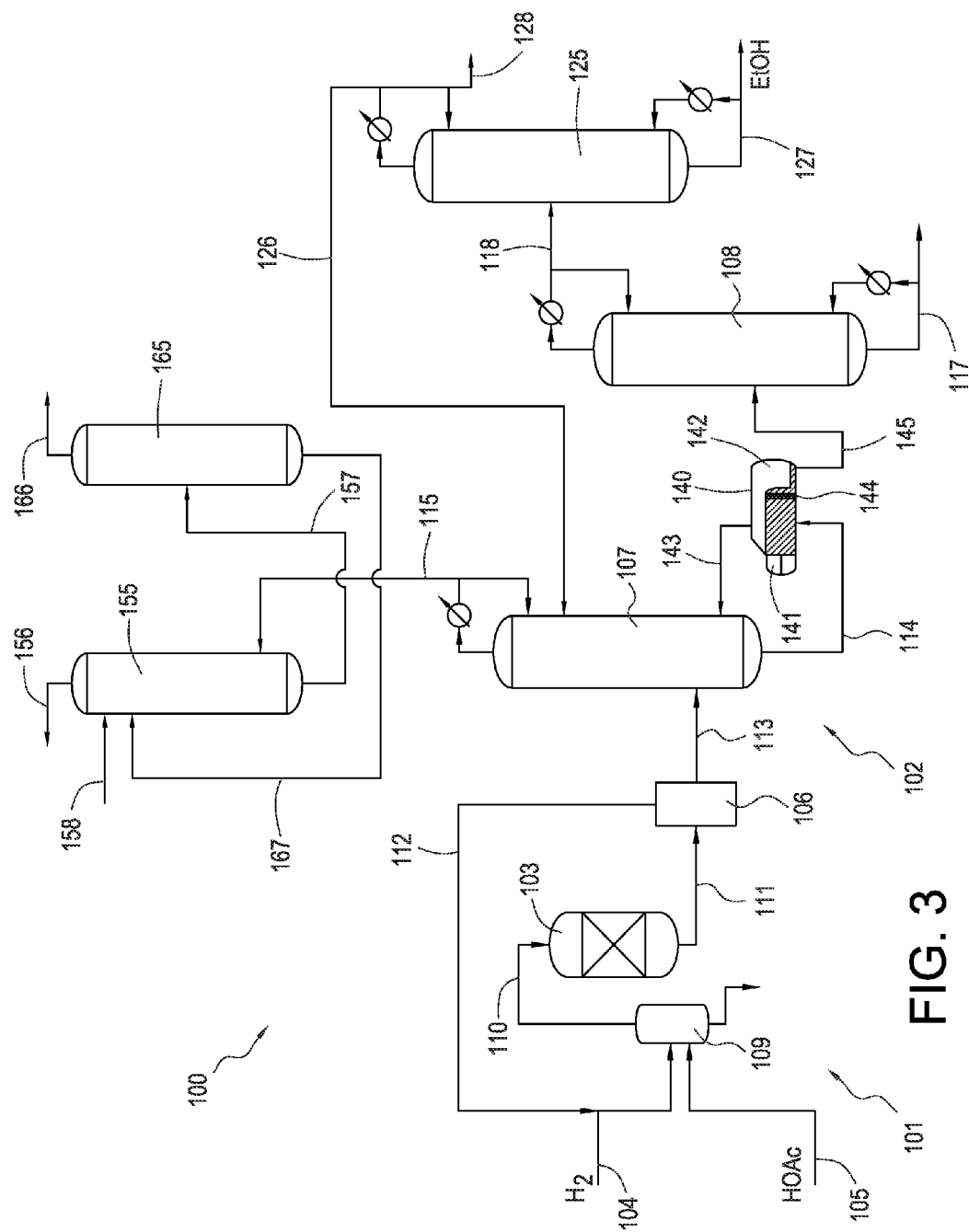
FIG. 3 is a schematic diagram of an ethanol production system with multiple distillation columns to recover ethanol, including an intervening ethanol separation in accordance with one embodiment of the present invention.
Figure 4:
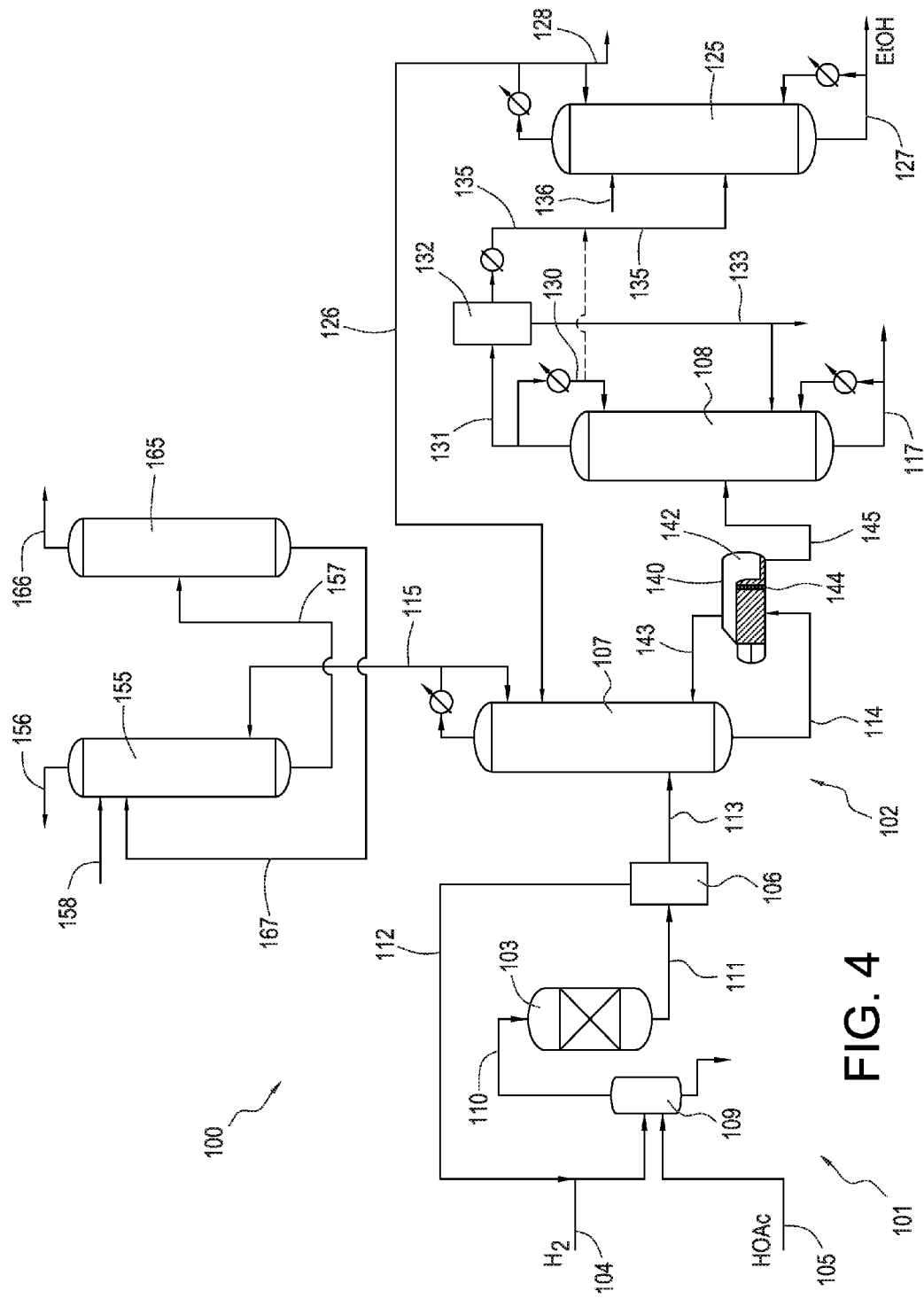
FIG. 4 is a schematic diagram of an ethanol production system with multiple distillation columns to recover ethanol including an intervening ethanol separation and an intervening water removal in accordance with one embodiment of the present invention.

In some embodiments, first distillate in stream 115 also comprises ethanol. Returning the ethanol may require an increase in reactor 103 capacity to maintain the same level of ethanol efficiency. To recover ethanol, first distillate in line 115 is fed, as is shown in FIGS. 3 and 4, to an extraction column 155 to recover ethanol and reduce the ethanol concentration recycled to reactor 103. Extraction column 155 may be a multi-stage extractor. In extraction column 155, the first distillate in line 115 is fed along with at least one extractant 158. In one embodiment, extractant 158 may be benzene, propylene glycol, and cyclohexane. Although water may be used, the extractant 158 preferably does not form an azeotrope with ethanol. A suitable extractant 158 is preferably non-carcinogenic and non-hazardous. Preferably, the extractant extracts ethanol from the first residue in line 157. The extractant may be recovered in recovery column 165 and returned via line 167. The ethanol stream in line 166 may be combined with ethanol product or returned to one of the distillation columns, such as first column 107. The raffinate 156 may be returned to reaction zone 101. Preferably, raffinate 156, which comprises acetaldehyde and ethyl acetate, is deficient in ethanol with respect to first distillate in line 115.

Exemplary components of the distillate and tower bottoms compositions for first column 107 are provided in Table 3 below. It should also be understood that the distillate and tower bottoms may also contain other components, not listed in Table 3. For convenience, the distillate and tower bottoms of the first column may also be referred to as the "first distillate" or "first bottoms." The distillates or residues of the other columns may also be referred to with similar numeric modifiers (second, third, etc.) in order to distinguish them from one another, but such modifiers should not be construed as requiring any particular separation order.

TABLE 3

EXTRACTIVE COLUMN

|  | Conc. (wt. %) | Conc. (wt. %) | Conc. (wt. %) |
|---|---|---|---|
| Distillate |  |  |  |
| Ethyl Acetate | 10 to 85 | 15 to 80 | 20 to 75 |
| Acetaldehyde | 0.1 to 70 | 0.2 to 65 | 0.5 to 65 |
| Acetal | <3 | 0.01 to 2 | 0.05 to 1.5 |
| Acetone | <0.05 | 0.001 to 0.03 | 0.01 to 0.025 |
| Ethanol | <25 | 0.001 to 20 | 0.01 to 15 |
| Water | 0.1 to 20 | 1 to 15 | 2 to 10 |
| Acetic Acid | <2 | <0.1 | <0.05 |
| Residue |  |  |  |
| Acetic Acid | 0.1 to 50 | 0.5 to 40 | 1 to 30 |
| Water | 20 to 85 | 25 to 80 | 30 to 75 |
| Ethanol | 10 to 75 | 15 to 70 | 20 to 65 |
| Ethyl Acetate | 0.001 to 1 | 0.01 to 0.5 | 0.01 to 0.1 |

In one embodiment of the present invention, first column 107 may be operated at a temperature where most of the water, ethanol, and acetic acid are removed as tower bottoms and only a small amount of ethanol and water is collected in the distillate stream due to the formation of binary and tertiary azeotropes. The weight ratio of water in the tower bottoms in line 114 to water in the distillate in line 115 may be greater than 1:1, e.g., greater than 2:1. The weight ratio of ethanol in the tower bottoms to ethanol in the distillate may be greater than 1:1, e.g., greater than 2:1.

The amount of acetic acid in the tower bottoms may vary depending primarily on the conversion in reactor 103. In one embodiment, when the conversion is high, e.g., greater than 90%, the amount of acetic acid in the tower bottoms may be less than 10 wt. %, e.g., less than 5 wt. % or less than 2 wt. %. In other embodiments, when the conversion is lower, e.g., less than 90%, the amount of acetic acid in the tower bottoms may be greater than 10 wt. %.

As shown in FIGS. 1-4, there is a kettle reboiler 140. A kettle type reboiler may be a shell and tube heat exchanger type. A heat source, e.g., steam, flows through the tubes (not shown) and exits the reboiler as a condensate. The tower bottoms in line 114 is fed into the bottom of the reboiler 140. The fluid in line 114, which may be pumped as necessary, may be at its saturation condition and all of the heat transferred to this fluid by heat source 141 may convert the liquid into vapors at the constant temperature. Heat source 141 may comprise one or more tubes (not shown) that extends into the liquid in the heating section. Vapors are collected in the disengagement space 142 and continuously fed to via the vapor return in line 143 to first column 107. The reboiled liquid that is not transferred to a vapor phase spills over a weir 144 separating the heating section from the collection section. The reboiled liquid may be withdrawn as the residue product in line 145 and may be continuously forwarded to second column 108. As explained herein, it is understood that other types of reboilers may be used and that FIGS. 1-4 show one exemplary process using a kettle reboiler. The residue product may be withdrawn from the base of first column 107 along with the tower bottoms in line 114.

Without being bound by theory, esterification of acetic acid and ethanol in the heating section and/or collection section may form additional ethyl acetate. It is believed that the esterification occurs in the liquid phase. In one embodiment to control the esterification and thus reduce ethyl acetate formation, reboiler 140 is operated to maintain low ethyl acetate formation and provide sufficient energy to drive separation in column 107. In one preferred embodiment, the amount of ethyl acetate in the residue product in line 145 preferably contains less than 1.5 wt. % ethyl acetate, e.g., less than 1.1 wt. % ethyl acetate based on the total weight of the residue product. When additional ethyl acetate is produced, it may be more difficult to remove the ethyl acetate from the ethanol product.

The first distillate in line 115 preferably is substantially free of acetic acid, e.g., comprising less than 1000 wppm, less than 500 wppm or less than 100 wppm acetic acid. The distillate may be purged from the system or recycled in whole or part to reactor 103. In some embodiments, when the distillate comprises ethyl acetate and acetaldehyde, the distillate may be further separated, e.g., in a distillation column (not shown) into an acetaldehyde stream and an ethyl acetate stream. The ethyl acetate stream may also be hydrolyzed or reduced with hydrogen, via hydrogenolysis, to produce ethanol. Either of these streams may be returned to the reactor 103 or separated from system 100 as additional products.

Some species, such as acetals, may decompose in first column 107 so that very low amounts, or even no detectable amounts, of acetals remain in the distillate or tower bottoms.

In addition, an equilibrium reaction between acetic acid/ethanol and ethyl acetate may occur in the crude ethanol product after exiting reactor 103 or first column 107 from reboiler in line 145. Depending on the concentration of acetic acid in the crude ethanol product, this equilibrium may be driven toward formation of ethyl acetate. This reaction may be regulated through the residence time and/or temperature of the crude ethanol product.

To recover ethanol, the residue product in line 145 may be further separated depending on the concentration of acetic acid and/or ethyl acetate. In most embodiments of the present invention, residue product in line 145 is further separated in a second column 108. The second column is referred to as an "acid separation column," because the second residue 117 comprises acetic acid and water. As shown in FIGS. 1 and 3, second column 108 yields a second residue in line 117 comprising acetic acid and water, and a second distillate in line 118 comprising ethanol and ethyl acetate. In one embodiment, a weight majority of the water and/or acetic acid fed to second column 108 is removed in the second residue in line 117, e.g., at least 60% of the water and/or acetic acid is removed in the second residue in line 117 or more preferably at least 80% of the water and/or acetic acid. An acid column may be desirable, for example, when the acetic acid concentration in the first residue is greater 50 wppm, e.g., greater than 0.1 wt. %, greater than 1 wt. %, e.g., greater than 5 wt. %.

In one embodiment first residue in line 145 may be preheated prior to being introduced into second column 108. The first residue in line 145 may be heat integrated with either the residue of the second column 108 or vapor overhead of second column 108. For purposes of the present invention, when preheating it is preferred than less than 30 mol. % of first residue in line 145 is in the vapor phase, e.g., less than 25 mol. % or less than 20 mol. %. Greater vapor phase contents result in increased energy consumption and a significant increase in the size of second column 108.

Optionally, further esterifying the acetic acid in residue product in line 145 may increase the ethyl acetate concentration which leads to increases in the size of second column 108 as well increases in reboiler duty. Thus, the conversion of acetic acid may be controlled depending on the initial ethyl acetate concentration withdrawn from first column. To maintain an efficient separation, the ethyl acetate concentration of the residue product in line 145 fed to second column 108 is preferably less than 1000 wppm, e.g., less than 800 wppm or less than 600 wppm.

Second column 108 operates in a manner to concentrate the ethanol from first residue so that a majority of the ethanol is carried overhead. Thus, the residue of second column 108 may have a low ethanol concentration of less than 5 wt. %, e.g. less than 1 wt. % or less than 0.5 wt. %. Lower ethanol concentrations may be achieved without significant increases in reboiler duty or column size. Thus, in some embodiments it is efficient to reduce the ethanol concentration in the residue to less than 50 wppm, or more preferably less than 25 wppm. As described herein, the residue of second column 108 may be treated and lower concentrations of ethanol allow the residue to be treated without generating further impurities.

The residue product in line 145 is introduced to second column 108, e.g., acid separation column, preferably in the top part of column 108, e.g., top half or top third. Feeding residue product in line 145 in a lower portion of second column 108 may unnecessarily increase the energy requirements of second column. Acid column 108 may be a tray column or packed column. Second column 108 may be a tray column having from 10 to 110 theoretical trays, e.g. from 15 to 95 theoretical trays or from 20 to 75 theoretical trays. Additional trays may be used if necessary to further reduce the ethanol concentration in the residue. In one embodiment, the reboiler duty and column size may be reduced by increasing the number of trays. In FIGS. 1 and 3, second column 108 yields a second residue in line 117 comprising acetic acid and water, and a second distillate in line 118 comprising ethanol.

Although the temperature and pressure of second column 108 may vary, when at atmospheric pressure the temperature of the second residue in line 117 preferably is from 95° C. to 160° C., e.g., from 100° C. to 150° C. or from 110° C. to 145° C. In one embodiment, when the residue product in line 145 is preheated to a temperature that is within 20° C. of the temperature of second residue in line 117, e.g., within 15° C. or within 10° C. The temperature of the second distillate exiting in line 118 from second column 130 preferably is from 50° C. to 120° C., e.g., from 75° C. to 118° C. or from 80° C. to 115° C. The temperature gradient may be sharper in the base of second column 108.

The pressure of second column 108 may range from 0.1 kPa to 510 kPa, e.g., from 1 kPa to 475 kPa or from 1 kPa to 375 kPa. In one embodiment, second column 108 operates above atmospheric pressure, e.g., above 170 kPa or above 375 kPa. Second column 108 may be constructed of a material such as 316L SS, Allot 2205 or Hastelloy C, depending on the operating pressure. The reboiler duty and column size for second column 108 remain relatively constant until the ethanol concentration in the second distillate in line 131 or 118 is greater than 90 wt. %.

Figure 2:
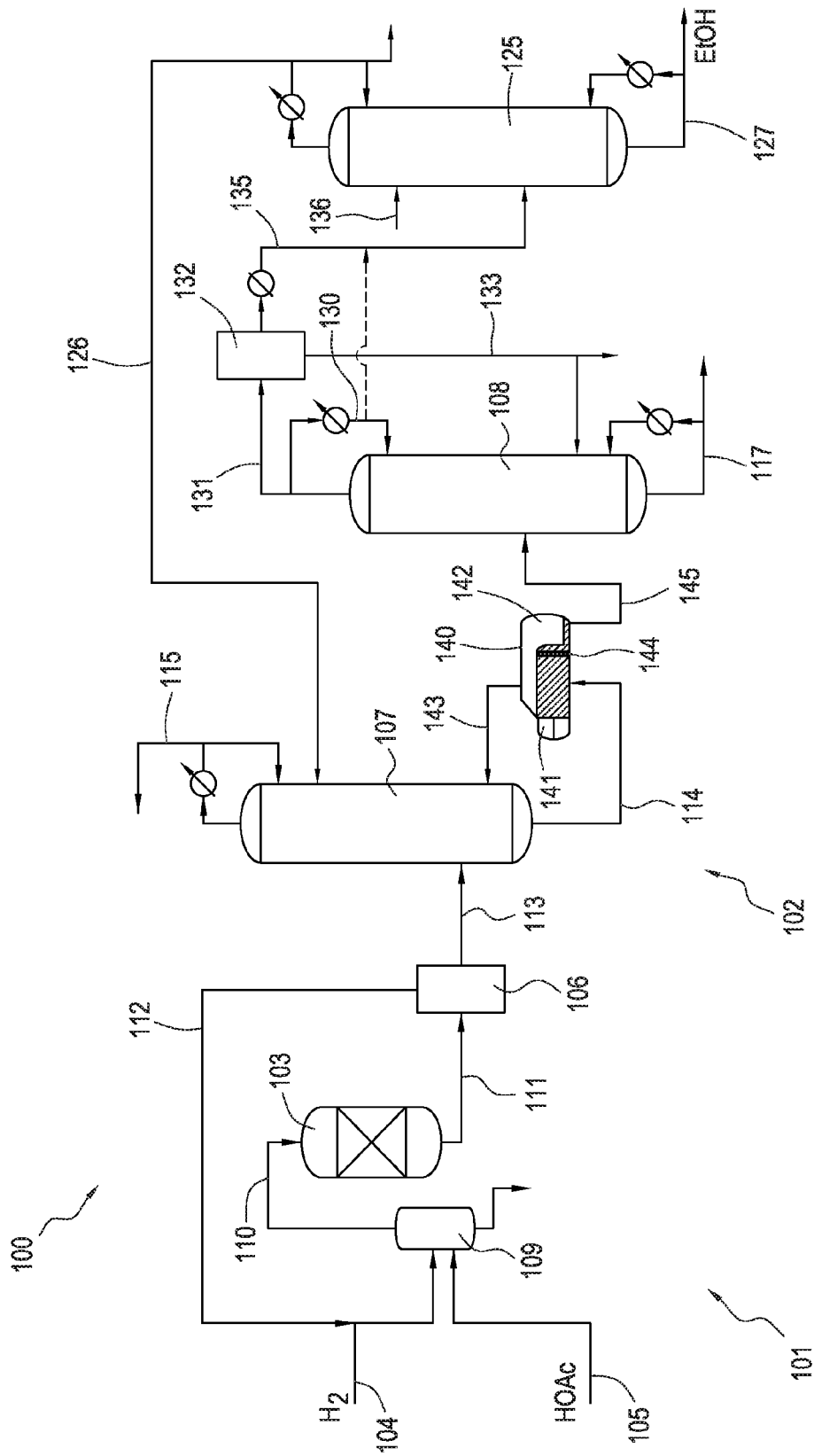
FIG. 2 is a schematic diagram of an ethanol production system with multiple distillation columns to recover ethanol including an intervening water removal in accordance with one embodiment of the present invention.

In one embodiment, water may be removed prior to recovering the ethanol product. In FIGS. 2 and 4, second column 108 yields a second residue in line 117 comprising acetic acid and water, and a second distillate in line 131 comprising ethanol. In one embodiment, the overhead in line 131 may comprise less than 15 wt. % water, e.g., less than 10 wt. % water or less than 8 wt. % water. As shown in FIGS. 2 and 4, overhead vapor in line 131 may be fed to water separator 132, which may be an adsorption unit, membrane, molecular sieves, extractive column distillation, or a combination thereof. In one embodiment, at least 50% of overhead vapor is fed to water separator 132, e.g., at least 75% or at least 90%. Optionally, some of overhead vapor in line 131 is condensed as second distillate 130 and optionally may be fed directly to third distillation column 125.

Water separator 132 in FIGS. 2 and 4 may be a pressure swing adsorption (PSA) unit. For purposes of clarity the details of the PSA unit are not shown in the figures. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separator 132 may remove at least 95% of the water overhead vapor 131, and more preferably from 95% to 99.99% of the water from vapor overhead 131, into a water stream 133. All or a portion of water stream 133 may be returned to second column 108, which may increase the reboiler duty and/or size of second column 108. Additionally or alternatively, all or a portion of water stream 133 may be purged. The remaining portion of vapor overhead 131 exits the water separator 132 as ethanol mixture stream 135. In one embodiment, ethanol mixture stream 135 comprises more than 92 wt. % ethanol, e.g., more than 95 wt. % or more than 99 wt. %. In one embodiment a portion of water stream 133 may be fed to first column 107 as the extractive agent.

A portion of vapor overhead 131 may be condensed and refluxed to second column 108, as shown, for example, at a ratio from 12:1 to 1:12, e.g., from 10:1 to 1:10 or from 8:1 to 1:8. The second distillate in line 130 optionally may be mixed with ethanol mixture stream 135 and co-fed to light ends column 125. This may be necessary if additional water is needed to improve separation in light ends column 125. It is understood that reflux ratios may vary with the number of stages, feed locations, column efficiency and/or feed composition. Operating with a reflux ratio of greater than 3:1 may be less preferred because more energy may be required to operate second column 108.

Exemplary components for the ethanol mixture of FIGS. 2 and 4, and residue compositions for second column 108 are provided in Table 4 below. It should be understood that the distillate and residue may also contain other components, not listed in Table 4. For example, in optional embodiments, when ethyl acetate is in the feed to reactor 103, second residue in line 117 exemplified in Table 4 may also comprise high boiling point components.

TABLE 4

ACID COLUMN

|  | Conc. (wt. %) | Conc. (wt. %) | Conc. (wt. %) |
|---|---|---|---|
| Ethanol Mixture Stream |  |  |  |
| Ethanol | 90 to 99.9 | 92 to 99 | 96 to 99 |
| Ethyl Acetate | <10 | 0.001 to 5 | 0.005 to 4 |
| Acetaldehyde | <10 | 0.001 to 5 | 0.005 to 4 |
| Water | <10 | 0.001 to 3 | 0.01 to 1 |
| Acetal | <2 | 0.001 to 1 | 0.005 to 0.5 |
| Second Residue |  |  |  |
| Acetic Acid | 0.1 to 45 | 0.2 to 40 | 0.5 to 35 |
| Water | 45 to 100 | 55 to 99.8 | 65 to 99.5 |
| Ethyl Acetate | <0.1 | 0.0001 to 0.05 | 0.0001 to 0.01 |
| Ethanol | <5 | 0.002 to 1 | 0.005 to 0.5 |

The weight ratio of ethanol in the ethanol mixture stream 135 to ethanol in the second residue in line 117 preferably is at least 35:1. Preferably, ethanol mixture stream 135 is substantially free of acetic acid and may contain, if any, trace amounts of acetic acid. A reduced concentration of acetic acid advantageously provides an ethanol product that also has no amount or a trace amount of acetic acid.

In one embodiment, ethyl acetate fed to second column 108 may concentrate in the vapor overhead and pass through with the ethanol mixture stream 135. Thus, preferably no ethyl acetate is withdrawn in the second residue in line 117. Advantageously this allows most of the ethyl acetate to be subsequently recovered without having to further process the second residue in line 117.

In optional embodiments, the feed to reactor 103 may comprise acetic acid and/or ethyl acetate. When ethyl acetate is used alone as a feed, the crude ethanol product may comprise substantially no water and/or acetic acid. There may be high boiling point components, such as alcohols having more than 2 carbon atoms, e.g., n-propanol, isopropanol, n-butanol, 2-butanol, and mixtures thereof. High boiling point components refer to compounds having a boiling point that is greater than ethanol. The high boiling point components may be removed in second column 108 in the second residue in line 117 described herein.

In one embodiment, due to the present of ethyl acetate formed in reboiler 140 that concentrates in ethanol mixture stream 135 in FIGS. 2 and 4 or second distillate in line 118 in FIGS. 1 and 3, an additional third column 125 may be used. A third column 125, referred to as a "light ends" column, is used for removing ethyl acetate from ethanol mixture stream 135 and producing an ethanol product in the third residue in line 127. Light ends column 125 may be a tray column or packed column. Third column 125 may be a tray column having from 5 to 90 theoretical trays, e.g. from 10 to 60 theoretical trays or from 15 to 50 theoretical trays.

The feed location of ethanol mixture stream 135 may vary depending on ethyl acetate concentration and it is preferred to feed ethanol mixture stream 135 to the upper portion of third column 125, e.g., upper third. Higher concentrations of ethyl acetate may be fed at a higher location in third column 125. However, the feed location should avoid the very top trays, near the reflux, to avoid excess reboiler duty requirements for the column and an increase in column size. For example, in a column having 45 actual trays, the feed location should be between 10 to 15 trays from the top. Feeding at a point above this may increase the reboiler duty and size of light ends column 125.

Ethanol mixture stream 135 or second distillate in line 118 may be fed to third column 125 at a temperature of up to 70° C., e.g., up to 50° C., or up to 40° C. In some embodiments it is not necessary to further preheat either ethanol mixture stream 135 or second distillate in line 118.

Ethyl acetate may be concentrated in the third distillate in line 128. Due to the relatively lower amounts of ethyl acetate fed to third column 125, third distillate in line 128 also comprises substantial amounts of ethanol. To recover the ethanol, third distillate in line 128 may be fed to first column as the ethyl acetate recycle stream 126. Because this increased the demands on the first and second columns, it is preferred that the concentration of ethanol in third distillate in line 128 be from 70 to 90 wt. %, e.g., from 72 to 88 wt. %, or from 75 to 85 wt. %.

In other embodiments, a portion of third distillate in line 128 may be purged from the system as a separate product, such as an ethyl acetate solvent.

In some embodiments to recover the ethanol without sending third distillate in line 128 back to first column 107, the ethanol may be recovered using an extractive column.

In an optional embodiment, the third residue may be further processed to recover ethanol with a desired amount of water, for example, using a further distillation column, adsorption unit, membrane or combination thereof, may be used to further remove water from third residue in line 127 as necessary. In most embodiments, the water is removed prior to third column 125 using water separator 132 and thus further drying of the ethanol is not required.

Third column 125 is preferably a tray column as described above and preferably operates at atmospheric pressure. The temperature of the third residue in line 127 exiting from third column 125 preferably is from 65° C. to 110° C., e.g., from 70° C. to 100° C. or from 75° C. to 80° C. The temperature of the third distillate in line 128 exiting from third column 125 preferably is from 30° C. to 70° C., e.g., from 40° C. to 65° C. or from 50° C. to 65° C.

The pressure of third column 125 may range from 0.1 kPa to 510 kPa, e.g., from 1 kPa to 475 kPa or from 1 kPa to 375 kPa. In some embodiments, third column 125 may operate under a vacuum of less than 70 kPa, e.g., less than 50 kPa, or less than 20 kPa. Decreases in operating pressure substantially decreases column diameter and reboiler duty for third column 125.

Exemplary components for ethanol mixture stream and residue compositions for third column 125 are provided in Table 5 below. It should be understood that the distillate and residue may also contain other components, not listed in Table 5.

TABLE 5

LIGHT ENDS COLUMN

|  | Conc. (wt. %) | Conc. (wt. %) | Conc. (wt. %) |
|---|---|---|---|
| Third Distillate | | | |
| Ethanol | 70 to 99 | 72 to 90 | 75 to 85 |
| Ethyl Acetate | 0.5 to 30 | 1 to 25 | 1 to 15 |
| Acetaldehyde | <15 | 0.001 to 10 | 0.1 to 5 |
| Water | <10 | 0.001 to 2 | 0.01 to 1 |
| Acetal | <2 | 0.001 to 1 | 0.01 to 0.5 |
| Third Residue | | | |
| Ethanol | 80 to 99.5 | 85 to 97 | 90 to 95 |
| Water | <8 | 0.001 to 3 | 0.01 to 1 |
| Ethyl Acetate | <1 | 0.0001 to 2 | 0.001 to 0.5 |
| Acetic Acid | <0.5 | <0.01 | 0.01 0.01 |

When first residue in line 145 comprise low amounts of acetic acid and/or there is no esterification of first residue, so that the ethyl acetate concentration is less than 50 wppm, third column 125 may be optional and removed. Thus, ethanol mixture stream 135 from the water separator 132 may be the ethanol product and there is no ethyl acetate recycle stream.

Depending on the amount of water and acetic acid contained in the second residue of second column 108, line 117 may be treated in one or more of the following processes. A suitable weak acid recovery system is described in US Pub. No. 2012/0010446, the entire contents and disclosure of which is hereby incorporated by reference. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from residue product in line 145 having a lower acetic acid concentration. The residue product in line 145 may be separated into acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent or to hydrolyze an ester-containing stream in a hydrolysis unit.

In other embodiments, for example where second residue in line 117 comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue in line 113 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. % or less than 1 wt. %, the residue may be neutralized and/or diluted before being disposed of to a waste water treatment facility. The organic content, e.g., acetic acid content, of the residue beneficially may be suitable to feed microorganisms used in a waste water treatment facility.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The ethanol product produced by the process of the present invention may be an industrial grade ethanol or fuel grade ethanol. Exemplary finished ethanol compositional ranges are provided below in Table 6.

TABLE 6

FINISHED ETHANOL COMPOSITIONS

| Component | Conc. (wt. %) | Conc. (wt. %) | Conc. (wt. %) |
|---|---|---|---|
| Ethanol | 85 to 99.9 | 90 to 99.5 | 92 to 99.5 |
| Water | <8 | 0.1 to 3 | 0.1 to 1 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, comprising:
   hydrogenating acetic acid and/or an ester thereof in a reactor in the presence of a catalyst to form a crude ethanol product;
   separating at least a portion of the crude ethanol product in a first distillation column to yield a first distillate comprising acetaldehyde and ethyl acetate and a tower bottoms comprising ethanol, acetic acid and water;
   feeding a first portion of the tower bottoms to a reboiler to generate a reboiler vapor stream;
   withdrawing a second portion of the tower bottoms as a residue product comprising less than 1.5 wt. % ethyl acetate;
   separating at least a portion of the residue product in a second distillation column to yield a second residue comprising acetic acid and water and a second distillate comprising ethanol and ethyl acetate; and
   separating at least a portion of the second distillate to yield a third residue comprising ethyl acetate and a third residue comprising ethanol.

2. The process of claim 1, wherein at least 50% of the ethanol in the crude ethanol product is withdrawn into the tower bottoms.

3. The process of claim 1, wherein the residue product comprises less than 1.1 wt. % ethyl acetate.

4. The process of claim 1, wherein the first portion of the tower bottoms comprises less than 1 wt. % ethyl acetate.

5. The process of claim 1, further comprising returning at least a portion of the third distillate to the first distillation column.

6. The process of claim 1, further comprising returning at least a portion of the first distillate to the reactor.

7. The process of claim 1, wherein the first distillate is further separated to yield an ethanol stream and a raffinate stream comprising ethyl acetate, and at least a portion of the raffinate stream is returned to the reactor.

8. The process of claim 7, wherein at least a portion of the ethanol stream is fed to the third distillation column.

9. The process of claim 1, wherein the reboiler is selected from the group consisting of internal reboiler, kettle reboiler, jacketed kettle reboiler, thermosyphon reboiler, falling film reboiler, fire reboiler, and forced circulation reboiler.

10. The process of claim 1, wherein the second distillate is further separated to yield an ethanol stream and a raffinate stream comprising ethyl acetate.

11. The process of claim 1, wherein the third distillate is further separated to yield an ethanol stream and a raffinate stream comprising ethyl acetate.

12. The process of claim 1, wherein the second distillate is substantially free of acetic acid.

13. The process of claim 1, further comprising removing water from at least a portion of the second distillate using an adsorption unit, membrane, extractive column distillation, molecular sieve, or a combination thereof to yield an ethanol product stream having a lower water content than the at least a portion of the second distillate.

14. The process of claim 13, wherein the third residue comprises less than 8 wt. % water.

15. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

16. A process for producing ethanol, comprising:
    hydrogenating acetic acid and/or an ester thereof in a reactor in the presence of a catalyst to form a crude ethanol product;
    separating at least a portion of the crude ethanol product in a first distillation column to yield a first distillate comprising acetaldehyde and ethyl acetate and a tower bottoms comprising ethanol, acetic acid, and water;
    feeding the tower bottoms to a reboiler to generate a reboiler vapor stream, and a residue product, wherein ethyl acetate is formed in the reboiler and the residue product comprises less than 1.5 wt. % ethyl acetate;
    separating at least a portion of the residue product in a second distillation column to yield a second residue comprising acetic acid and water and a second distillate comprising ethanol, and ethyl acetate; and
    separating at least a portion of the second distillate to yield a third distillate comprising ethyl acetate and a third residue comprising ethanol.

17. A process for producing ethanol comprising:
    hydrogenating acetic acid and/or an ester thereof in a reactor in the presence of a catalyst to form a crude ethanol product;
    separating a portion of the crude ethanol product in a first distillation column to yield a first distillate comprising acetaldehyde and ethyl acetate and a tower bottoms comprising ethanol, acetic acid and water;
    feeding the tower bottoms to a reboiler to generate a reboiler vapor stream, and a residue product, wherein ethyl acetate is formed in the reboiler and the residue product comprises less than 1.5 wt. % ethyl acetate;
    separating a portion of the residue product in a second distillation column to yield a second residue comprising acetic acid and a second distillate comprising ethanol, ethyl acetate and water;
    removing water from at least a portion of the second distillate to yield an ethanol product stream having a lower water content than the at least a portion of the second distillate; and
    separating at least a portion of the ethanol product stream in a third distillation column to yield a third distillate comprising ethyl acetate and a third residue comprising ethanol and less than 8 wt. % water.

18. The process of claim 17, wherein removing water using an adsorption unit, membrane, extractive column distillation, molecular sieves, or a combination thereof.

19. A process for producing ethanol comprising:
    hydrogenating acetic acid and/or an ester thereof in a reactor in the presence of a catalyst to form a crude ethanol product;
    separating a portion of the crude ethanol product in a first distillation column to yield a first distillate comprising acetaldehyde and ethyl acetate and a tower bottoms comprising ethanol, and acetic acid;
    feeding the tower bottoms to a reboiler to generate a reboiler vapor stream, and a residue product, wherein ethyl acetate is formed in the reboiler and the residue product comprises less than 1.5 wt. % ethyl acetate;
    separating a portion of the residue product in a second distillation column to yield a second residue comprising high boiling point components and a second distillate comprising ethanol and ethyl acetate; and
    separating at least a portion of the second distillate to yield a third distillate comprising ethyl acetate and a third residue comprising ethanol;
    wherein the residue product comprises more ethyl acetate than the tower bottoms.

20. The process of claim 19, wherein the high boiling point components are selected from the group consisting of acetic acid, water, alcohols having more than 2 carbon atoms, and mixtures thereof.

* * * * *